United States Patent [19]

Jakobson et al.

[11] Patent Number: 5,041,688
[45] Date of Patent: Aug. 20, 1991

[54] PROCESS FOR THE PREPARATION OF POLYGLYCEROLS

[75] Inventors: Gerald Jakobson; Werner Siemanowski, both of Rheinberg, Fed. Rep. of Germany

[73] Assignee: Deutsche Solvay-Werke GmbH, Solinger, Fed. Rep. of Germany

[21] Appl. No.: 452,509

[22] Filed: Dec. 19, 1989

[30] Foreign Application Priority Data

Dec. 19, 1988 [DE] Fed. Rep. of Germany ....... 3842692

[51] Int. Cl.$^5$ ............................................. C07C 41/03
[52] U.S. Cl. .................................... 568/620; 568/621; 568/679; 568/680
[58] Field of Search ................. 568/620, 621, 679, 680

[56] References Cited

U.S. PATENT DOCUMENTS 2,260,753  10/1941  Marple et al. ...................... 568/614
2,520,670   8/1950  Wittcoff et al. .................... 260/615

FOREIGN PATENT DOCUMENTS 3410520  9/1985  Fed. Rep. of Germany ...... 518/679

Primary Examiner—Howard T. Mars
Attorney, Agent, or Firm—Foley & Lardner

[57] ABSTRACT

The invention relates to a process for the preparation of polyglycerols (with more than 50% by weight of diglycerol) which are low in cyclic components, by reacting glycerol with chlorohydrins. In this reaction, glycerol is reacted with epichlorohydrin (instead of chlorohydrin) at temperatures from 20° to 120° C. and at certain mole ratios of glycerol to epichlorohydrin and in the presence of an acidic catalyst and the reaction mixture obtained, which has not been separated into its components, is reacted at a temperature from 50° C. to 120° C. according to the content of organically bound chlorine in the reaction mixture, with an alkaline-reacting, preferably aqueous solution. After the addition of water, the reaction mixture is desalinated via one or more cation and subsequent anion exchangers, dehydrated by distillation and the glycerol-polyglycerol mixture obtained is separated by fractional distillation into glycerol, diglycerol and higher polyglycerols.

22 Claims, No Drawings

PROCESS FOR THE PREPARATION OF POLYGLYCEROLS

BACKGROUND OF THE INVENTION

The present invention relates to a process for the preparation of polyglycerols, with more than 50% by weight of diglycerol, which are low in cyclic components, by reacting glycerol with chlorohydrins.

A process of this type has already been disclosed in U.S. Pat. No. 2,520,670, by which glycerol is reacted with glycerol α-monochlorohydrin in the presence of concentrated alkali at elevated temperature to form a mixture of polyglycerols. This process has the disadvantage of a relatively long reaction time and a high proportion of polyglycerols. Moreover, after conclusion of the reaction the reaction mixture has to be worked up with lower aliphatic alcohols.

Data concerning the yields of polyglycerols achieved or the content of cyclic components in the latter are not given.

SUMMARY OF THE INVENTION

Accordingly, it is an object of the present invention to provide a process for producing polyglycerols (with more than 50% by weight of diglycerol) in good yields and with only a small proportion of cyclic components.

Another object of the present invention is to provide a process for producing polyglycerols which does not require simultaneous isolation of the intermediates (chlorohydrin ether mixture) and which is environmentally advantageous in not requiring work up of the end products by treatment with organic solvents.

A further object of the present invention is to provide a process which can be carried out at relatively low temperatures.

In accomplishing the foregoing objectives, there has been provided, in accordance with one aspect of the present invention, a process for the preparation of polyglycerols which are low in cyclic components, which comprises the steps of: reacting glycerol with epichlorohydrin in a molar ratio of about 3:1 to 1:1 at a temperature from about 20° to 140° C. in the presence of an acidic catalyst to produce a first reaction mixture; reacting the first reaction mixture, without separation of the components thereof, at a temperature from about 50° to 120° C., with an alkaline-reacting medium according to the content of organically-bound chlorine in the mixture, to produce a second reaction mixture; diluting the second reaction mixture with water to form an aqueous solution; desalinating the solution by passing it through at least one cation exchanger followed by at least one anion exchanger; dehydrating the solution by distillation to produce a glycerol-polyglycerol mixture; and separating the glycerol-polyglycerol mixture by fractional distillation into glycerol, diglycerol and higher polyglycerols, wherein the weight content of diglycerol in the polyglycerol mixture is at least 50%.

Other objects, features and advantages of the present invention will become apparent to those skilled in the art from the following detailed description. It should be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

According to the invention, polyglycerols (with more than 50% by weight of diglycerol) are produced by reacting glycerol with epichlorohydrin (instead of chlorohydrin) at temperatures from about 20° to 140° C., preferably from 60° C. to 100° C., in the presence of an acidic catalyst and a mole ratio of glycerol to epichlorohydrin of about 10:1 to 1:1 and reacting the reaction mixture obtained, which has not been separated into components, at a temperature from about 50° C. to 120° C., preferably from 80° C. to 95° C., according to the content of organically bound chlorine in the reaction mixture, with an alkaline reacting medium, preferably an alkaline-reacting aqueous solution, desalinating the reaction mixture after the addition of water via one or more cation exchangers and subsequently with the use of anion exchangers, dehydrating the mixture by distillation and separating the glycerol-polyglycerol mixture by fractional distillation into glycerol, diglycerol and higher polyglycerols.

In the reaction of glycerol, it is preferable to use an acid as acidic catalyst, preferably sulfuric acid, perchloric acid, phosphoric acid and/or phosphorous acid.

The acid used as acidic catalyst is added in a concentration of about 0.1 to 2.0% by weight, preferably of 0.5 to 1.2% by weight, relative to the epichlorohydrin used.

According to an advantageous embodiment of the invention, the reaction mixture is diluted by the addition of water to an approximately 70-40% by weight strength solution, preferably 60-50% by weight strength solution, and desalinated at temperatures from about 30° C. to 90° C., preferably from 40° C. to 70° C., via a combination of strongly acidic cation exchangers and subsequent weakly basic anion exchangers.

According to a preferred embodiment, an alkaline-reacting alkali metal carbonate solution, preferably a concentrated sodium carbonate solution, is added to the reaction mixture from the reaction of epichlorohydrin with glycerol, which has not been separated into its components.

The reaction mixture from the reaction of epichlorohydrin with glycerol which has not been separated into its components, is advantageously added to an alkaline-reacting alkali metal carbonate solution, the ratio of equivalents of the alkali metal carbonate to the content of organically bound chlorine being about 1:1 to 1.2:1, preferably 1.05:1 to 1.1:1.

The reaction mixture is expediently adjusted to a pH range of about 7.0 to 11.5, preferably 8 to 11, by means of the alkaline-reacting aqueous solution.

According to a further embodiment, the reaction mixture is cooled to room temperature and the bulk of the precipitated salt is separated, preferably filtered off.

In order to increase the proportion of diglycerol, the mole ratio of glycerol to epichlorohydrin is advantageously about 10:1 to 1:1, preferably 6.0.:1 to 1.7:1.

According to another embodiment, the alkaline-reacting alkali metal carbonate solution is added in low excess to the reaction mixture from the reaction of epichlorohydrin with glycerol, which has not been separated into its components, and after the reaction has been completed, this excess is neutralized.

Hydrochloric acid is preferably used for the neutralization, but other mineral acids or acidic cation exchangers may also be used.

It has furthermore been established according to the invention that changing the mole ratios is accompanied by a change in the reaction time. With regard to the reaction time, to the high proportion of diglycerol/polyglycerol desired minimum content of cyclic components in the crude polyglycerol mixture, a mole ratio of glycerol to epichlorohydrin of about 2.0 to 1.5:1 has proved particularly favorable.

The regeneration of the cation exchange medium in the cation exchangers is preferably carried out by means of co-current regeneration or compound-co-current regeneration.

According to a preferred embodiment, after the regeneration, the salts are washed out. After the washing out procedure has been concluded, the polyglycerol-containing, preferably diglycerol-containing solution is passed through the ion exchangers and the polyglycerol-containing, preferably diglycerol-containing solution leaving the anion exchanger is fed back until a polyglycerol content, preferably a diglycerol content, of about 20% by weight has been achieved, preferably until a polyglycerol content, preferably diglycerol content of 15% by weight has been achieved, and is concomitantly used for the preparation of the approximately 70–40% by weight strength, preferably 60–50% by weight strength polyglycerol-containing, preferably diglycerol-containing starting solution.

Passing the polyglycerol-containing, preferably diglycerol-containing solution through the ion exchangers is preferably carried out using an excess pressure.

In this procedure, the polyglycerol-containing, preferably diglycerol-containing solution is passed through the ion exchangers, i.e. through one or more cation exchangers and at least one anion exchanger at a pressure of about 1.1–8 bar, preferably 1.5–5 bar. In order and maintain the pressure, valves are fitted at one or more positions in the pipework or on the ion exchangers.

During this procedure, the polyglycerol-containing, preferably diglycerol-containing solution is expediently passed through the ion exchangers with a flow rate of about 0.5 m/h to 15 m/h, preferably 1 m/h to 5 m/h.

Cation exchange media and anion exchange media used are preferably those which are heat resistant up to above 80° C., preferably up to above 100° C.

The ion exchange medium of the cation exchanger and/or anion exchanger is expediently covered by a sieve plate, perforated plate or by a device arranged displaceably in the upward direction of the ion plate, perforated plate or by a device arranged displaceably in the upward direction of the ion exchanger, covering the exchange medium and allowing a uniform liquid throughput to be achieved, and/or covered by an inert molding composition and/or elastic plastic composition.

The strongly acidic cation exchange medium and the weakly basic anion exchange medium preferably have an internal surface (measured by the BET method) of more than 25 $m^2/g$, preferably 50 to 100 $m^2/g$.

EXEMPLARY EMBODIMENT

Preparation of polyglycerol with a relatively high proportion of diglycerol:

0.925 kg (10 mol) of glycerol and 3.5 ml of concentrated sulfuric acid are initially introduced into a 2 l jacketed reactor (temperature control medium: oil). 0.639 kg (6.9 mol) of epichlorohydrin are added with stirring at a rate such that the reaction temperature remains below 90° C. (if necessary the temperature control oil is cooled via a heat exchanger). After addition for about 2 hours the batch is stirred for a further 15 min for completion of the reaction.

Weight of crude product: 1.5 kg 1.898 1 of a 2 molar sodium carbonate solution (corresponding to the content of organically bound chlorine from the aforesaid reaction plus a 10% excess) are heated to about 90° C. The chlorohydrin ether mixture which has not been further worked up is added dropwise to this alkaline solution with stirring over a period of 2 h. After a further 30 minutes at this temperature the heating is switched off and the reaction mixture is neutralized by the addition of ½ concentrated hydrochloric acid. The neutral reaction solution is concentrated in vacuo, the precipitated salts filtered off and the filtrate desalinated after dilution with water, via a combination of cation and anion exchangers. This crude polyglycerol solution is evaporated in vacuo in order to dehydrate it.

The product mixture had the following composition (in % by weight): glycerol 36.3% by weight, cyclic diglycerol 0.9% by weight, diglycerol 42.0% by weight, cyclic triglycerol 0.4% by weight, triglycerol 15.2% by weight, cyclic tetraglycerol 0.3% by weight, tetraglycerol 4.5% by weight, pentaglycerol 0.4% by weight.

What is claimed is:

1. A process for the preparation of polyglycerols which are low in cyclic components, which comprises the steps of:
   (a) reacting glycerol with epichlorohydrin in a molar ratio of about 2.0:1 to 1.5:1 at a temperature from about 20 to 140° C. in the presence of sulfuric acid, perchloric acid, phosphoric acid, phosphorous acid or a mixture thereof in a concentration of about 0.1 to 2.0 wt% relative to the epichlorohydrin used to produce a first reaction mixture;
   (b) reacting said first reaction mixture, without separation of the components of said mixture, at a temperature from about 50 to 120° C. with an alkaline-reacting alkali metal carbonate solution according to the content of organically-bound chlorine in said first reaction mixture, wherein the ratio of equivalents of the alkali metal carbonate to the content of organically bound chlorine is about 1:1 to 1.2:1, to produce a second reaction mixture, followed by neutralization of the excess alkali metal carbonate after completion of the reaction;
   (c) concentrating said second reaction mixture;
   (d) filtering off salts precipitated in step (c) from said second reaction mixture;
   (e) diluting said second reaction mixture with water to form an aqueous solution, wherein said aqueous solution has a glycerol-polyglycerol concentration is 60 to 50 wt%;
   (f) desalinating said solution by passing said solution through at least one cation exchanger followed by at least one anion exchanger at a temperature of 40 to 70° C.;
   (g) dehydrating said solution by distillation to produce a glycerol-polyglycerol mixture; and
   (h) separating said glycerol-polyglycerol mixture by fractional distillation into glycerol, diglycerol and higher polyglycerols, wherein the weight content of diglycerol in the polyglycerol mixture is at least about 50%.

2. A process as claimed in claim 1, wherein step (a) is carried out at a temperature of 60° to 100° C.

3. A process as claimed in claim 1, wherein said acid is added in a concentration of 0.5 to 1.2 wt% relative to the epichlorohydrin used.

4. A process as claimed in claim 1, wherein step (b) is carried out at a temperature of 80° to 95° C.

5. A process as claimed in claim 1, wherein said alkali metal carbonate solution is a concentrated sodium carbonate solution.

6. A process as claimed in claim 1, wherein said ratio is 1.05:1 to 1.1:1.

7. A process as claimed in claim 1, wherein said second reaction mixture is adjusted to a pH range of about 7.0 to 11.5 by means of the alkaline-reacting aqueous solution.

8. A process as claimed in claim 7, wherein said pH range is 8 to 11.

9. A process as claimed in claim 1, wherein desalination step (f) is carried out via a combination of a strongly acidic cation exchanger and a subsequent weakly basic anion exchanger.

10. A process as claimed in claim 1, further comprising the step of regenerating the cation exchange medium of said cation exchanger and washing the salts out of the cation exchanger after regeneration, wherein after said washing step, a portion of said aqueous solution is cycled through said ion exchangers until its total glycerol-polyglycerol concentration is reduced to about 20° by weight, after which the recycle effluent is used in step (c) to dilute more of said second reaction mixture and form said aqueous solution.

11. A process as claimed in claim 10 wherein said regeneration step is carried out by means of co-current regeneration or compound co-current regeneration.

12. A process as claimed in claim 10, wherein the total glycerol-polyglycerol content of said recycle effluent is reduced to about 15% by weight.

13. A process as claimed in claim 1, wherein said solution is passed through said ion exchangers under elevated pressure.

14. A process as claimed in claim 13, wherein said pressure is about 1.1 to 8 bar.

15. A process as claimed in claim 14, wherein said pressure is 1.5 to 5 bar.

16. A process as claimed in claim 1, wherein the ion exchange media in said cation exchanger and said anion exchanger are covered by a sieve plate, a perforated plate or a device disposed displaceably in the upward direction of the ion exchanger in order to facilitate uniform throughput of said aqueous solution, or by an inert molding material or an elastic plastic material.

17. A process as claimed in claim 1, wherein the ion exchange media in said cation exchanger and said anion exchanger are heat resistant up to a temperature of at least 80° C.

18. A process as claimed in claim 17, wherein said ion exchange media are heat resistant up to a temperature of at least 100° C.

19. A process as claimed in claim 1, wherein the ion exchange media in said cation exchanger and said anion exchanger each have an internal surface area, measured by the BET method, of at least 25 m$^2$/g.

20. A process as claimed in claim 19, wherein the ion exchange media in said cation exchanger and said anion exchanger each have an internal surface area, measured by the BET method, of about 50 to 100 m$^2$/g.

21. A process as claimed in claim 1, wherein said aqueous solution is passed through said ion exchangers at a flow rate of about 0.5 to 15 m/h.

22. A process as claimed in claim 21, wherein said flow rate is 1 to 5 m/h.

* * * * *